US00PP19497P2

(12) United States Plant Patent
Schräder

(10) Patent No.: US PP19,497 P2
(45) Date of Patent: Nov. 25, 2008

(54) ***LOBELIA* PLANT NAMED 'SUMLOB 02'**

(50) Latin Name: *Lobelia richardii*
Varietal Denomination: SUMLOB 02

(76) Inventor: Ralf Schräder, Karl-Leisner-Str. 15, D-59348 Lüdinghausen (DE)

( * ) Notice: Subject to any disclaimer, the term of this patent is extended or adjusted under 35 U.S.C. 154(b) by 0 days.

(21) Appl. No.: 12/011,393

(22) Filed: Jan. 25, 2008

(51) Int. Cl.
*A01H 5/00* (2006.01)

(52) U.S. Cl. ..... Plt./451

(58) Field of Classification Search ..... Plt./451
See application file for complete search history.

*Primary Examiner*—Annette H Para
(74) *Attorney, Agent, or Firm*—C. A. Whealy

(57) ABSTRACT

A new and distinct cultivar of *Lobelia* plant named 'Sumlob 02', characterized by its compact, spreading to cascading plant habit; vigorous growth habit; freely branching habit; long flowering period; continuously and freely flowering habit; dark blue-colored flowers with large white-colored eyes; and good garden performance.

1 Drawing Sheet

Botanical designation: *Lobelia richardii.*
Cultivar denomination: 'SUMLOB 02'.

BACKGROUND OF THE INVENTION

The present invention relates to a new and distinct cultivar of *Lobelia,* botanically known as *Lobelia richardii* and hereinafter referred to by the name 'Sumlob 02'.

The new *Lobelia* is a product of a planned breeding program conducted by the Inventor in Lüdinghausen, Germany. The objective of the breeding program is to create new *Lobelia* cultivars with cascading habit, long flowering period, tolerance to high temperatures and high light and blue-colored flowers.

The new *Lobelia* originated from a cross-pollination made by the Inventor in March, 2003 of a proprietary seedling selection of *Lobelia richardii* identified as code number Lo 12, not patented, as the female, or seed, parent with a proprietary seedling selection of *Lobelia richardii* identified as code number Lo 02, not patented, as the male, or pollen, parent. The new *Lobelia* was discovered and selected by the Inventor as a single flowering plant with the progeny of the stated cross-pollination in a controlled environment in Lüdinghausen, Germany in October 2003.

Asexual reproduction of the new cultivar by vegetative cuttings in Lüdinghausen, Germany since January, 2004, has shown that the unique features of this new *Lobelia* are stable and reproduced true to type in successive generations.

SUMMARY OF THE INVENTION

Plants of the cultivar Sumlob 02 have not been observed under all possible environmental conditions. The phenotype may vary somewhat with variations in environment such as temperature and light intensity without, however, any variance in genotype.

The following traits have been repeatedly observed and are determined to be the unique characteristics of 'Sumlob 02'. These characteristics in combination distinguish 'Sumlob 02' as a new and distinct cultivar of *Lobelia:*

1. Compact, spreading to cascading plant habit.
2. Vigorous growth habit.
3. Freely branching habit.

4. Long flowering period; continuously and freely flowering habit.
5. Dark blue-colored flowers with large white-colored eyes.
6. Good garden performance.

Plants of the new *Lobelia* differ from plants of the female parent selection in the following characteristics:

1. Plants of the new *Lobelia* have larger flowers than plants of the female parent selection.
2. Flowers of plants of the new *Lobelia* are darker blue in color than flowers of plants of the female parent selection.

Plants of the new *Lobelia* differ from plants of the male parent selection in the following characteristics:

1. Plants of the new *Lobelia* are more compact than plants of the male parent selection.
2. Plants of the new *Lobelia* are more freely branching than plants of the male parent selection.

Plants of the new *Lobelia* can be compared to plants of the cultivar Grülo 06, disclosed in U.S. Plant Pat. No. 18,045. In side-by-side comparisons conducted in Lüdinghausen, Germany, plants of the new *Lobelia* differed from plants of the cultivar Grülo 06 in the following characteristics:

1. Plants of the new *Lobelia* flowered about two weeks earlier than plants of the cultivar Grülo 06.
2. Plants of the new *Lobelia* were more compact than plants of the cultivar Grülo 06.
3. Plants of the new *Lobelia* had smaller leaves than plants of the cultivar Grülo 06.
4. Plants of the new *Lobelia* had larger flowers than plants of the cultivar Grülo 06.
5. Flowers of plants of the new *Lobelia* were darker blue in color than flowers of plants of the cultivar Grülo 06.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the actual colors of the new *Lobelia*. The photograph comprises a side perspective view of a typical flowering plant of 'Sumlob 02'.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photograph and following description were grown under conditions which closely approximate commercial production conditions during the spring and summer in an outdoor nursery in Lüdinghausen, Germany for about five months in containers. During the production of the plants, day temperatures ranged from 16° C. to 28° C., night temperatures ranged from 10° C., to 18° C. and light levels ranged from 25,000 lux to 45,000 lux. Plants were pinched one time shortly after planting.

Botanical classification: *Lobelia richardii* cultivar Sumlob 02.

Parentage:

*Female parent.*—Proprietary seedling selection of *Lobelia richardii* identified as code number Lo 12, not patented.

*Male parent.*—Proprietary seedling selection of *Lobelia richardii* identified as code number Lo 02, not patented.

Propagation:

*Type cutting.*—Vegetative cuttings.

*Time to initiate roots.*—About 12 to 16 days at 16° C.

*Time to produce a rooted young plant.*—About 24 to 30 days at 16° C.

*Root description.*—Fine, fibrous; 162C in color.

*Rooting habit.*—Freely branching; moderately dense.

Plant description:

*Form/growth habit.*—Compact, spreading to cascading plant habit. Freely branching habit with about ten to twelve lateral branches developing per plant. Vigorous growth habit.

*Plant height.*—About 25 cm.

*Plant width.*—About 25 cm to 30 cm.

*Lateral branch description.*—Length: About 25 cm to 30 cm. Diameter: About 1 mm to 1.5 mm. Internode length: About 2 cm to 3 cm. Strength: Strong. Texture: Smooth, glabrous. Color: 137A.

Foliage description:

*Arrangement.*—Alternate, simple.

*Length, basal leaves.*—About 3 cm to 3.5 cm.

*Width, basal leaves.*—About 2 cm to 2.4 cm.

*Length, mid-plant leaves.*—About 3.5 cm to 4 cm.

*Width, mid-plant leaves.*—About 1.6 cm to 1.8 cm.

*Shape, basal leaves.*—Elliptical to oval.

*Shape, mid-plant leaves.*—Lanceolate.

*Apex, all leaves.*—Acuminate.

*Base, all leaves.*—Attenuate.

*Margin all leaves.*—Crenate.

*Texture, all leaves, upper and lower surfaces.*—Smooth, glabrous.

*Venation pattern, all leaves.*—Pinnate.

*Color, all leaves.*—Developing foliage, upper surface: 137C. Developing foliage, lower surface: 138A. Fully expanded foliage, upper surface: 137B; venation, 138C. Fully expanded foliage, lower surface: 137C; venation, 138C.

*Petiole length.*—About 8 mm to 10 mm.

*Petiole diameter.*—About 2 mm.

*Petiole texture, upper and lower surfaces.*—Smooth, glabrous.

*Petiole color, upper and lower surfaces.*—138A.

Flower description:

*Flower arrangement/shape.*—Flowers arranged in terminal racemes. Flowers face upright to outwardly. Flowers not persistent. Flowering early, freely and continuously; older flowers are overgrown by new flowers and foliage; about 120 to 150 flowers develop per plant. Flowers not fragrant. Flowers with three larger lower petals and two smaller upper petals.

*Natural flowering season.*—Early spring until frost in Germany.

*Flower longevity on the plant.*—Longevity of individual flowers is highly dependent on weather conditions; typically about eight to ten days.

*Inflorescence height.*—About 10 cm to 12 cm.

*Inflorescence diameter.*—About 3 cm to 4 cm.

*Flower diameter.*—About 1.5 cm to 1.8 cm.

*Flower depth (height).*—About 1.7 cm.

*Flower buds.*—Length: About 1 cm to 1.2 cm. Diameter: About 2 mm to 4 mm. Shape: Oval. Color: 154D.

*Petals.*—Arrangement: Single whorl of five petals, fused; three larger lower petals and two smaller upper petals. Three lower petals: Length, above throat: About 1.5 cm to 1.6 cm. Width: About 5 mm to 7 mm. Two upper petals: Length, above throat: About 6 mm to 8 mm. Width: About 1 mm to 2 mm. Upper and lower petals: Shape: Obovate. Apex: Rounded. Margin: Entire. Texture, upper and lower surfaces: Smooth, glabrous. Color, upper and lower petals: When opening, upper surface: 96B. When opening, lower surface: 97B; towards the apex, 96D. Fully opened, upper surface: 96B to 96C; towards central circle, 95A; eye, 155A; color becoming closer to 95A with development. Fully opened, lower surface: Towards the apex, 95C; towards the base, 97D; stripes, 95D.

*Sepals.*—Arrangement: Single whorl of five sepals, fused at the base; star-shaped calyx. Length: About 8 mm to 10 mm. Width: About 1 mm. Shape: Lanceolate. Apex: Acute. Margin: Entire. Texture, upper and lower surfaces: Smooth, glabrous. Color, immature, upper and lower surfaces: 144A. Color, mature, upper and lower surfaces: 146A.

*Peduncles.*—Length: About 2 cm to 2.5 cm. Diameter: About 0.5 mm to 1 mm. Strength: Strong. Texture: Smooth, glabrous. Color: 137A.

*Reproductive organs.*—Stamens: Quantity per flower: About five. Anther length: About 2 mm. Anther color: N200C. Pollen amount: Moderate. Pollen color: 3B. Pistils: Quantity per flower: One. Pistil length: About 8 mm. Stigma shape: Rounded. Stigma color: N200B. Style length: About 1 mm. Style color: N200B. Ovary color: N200B.

*Seeds.*—Quantity per flower: About ten to twelve. Length: About 0.5 mm. Diameter: About 0.5 mm. Color: 200D.

Disease/pest resistance: Plants of the new *Lobelia* have not been noted to be resistant to pathogens and pests common to *Lobelia*.

Garden performance: Plants of the new *Lobelia* have been observed to have good garden performance and to tolerate rain, wind and temperatures ranging from about 0° C. to about 35° C. to 40° C.

It is claimed:

1. A new and distinct *Lobelia* plant named 'Sumlob 02' as illustrated and described.

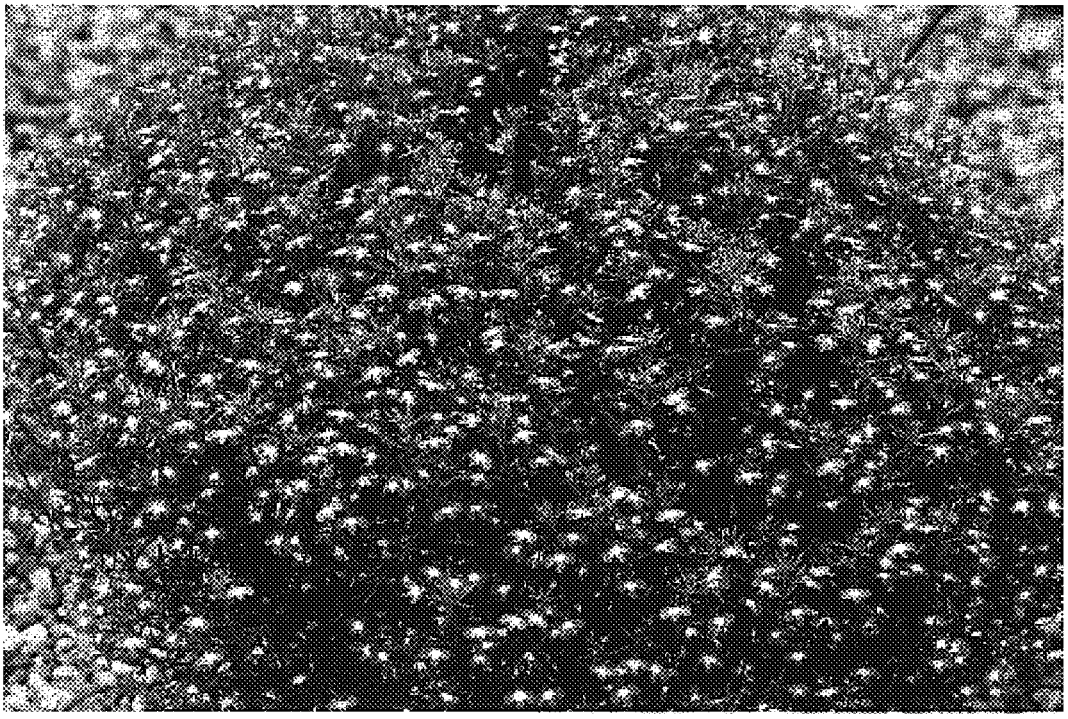

* * * * *